(12) United States Patent
Sorge et al.

(10) Patent No.: US 7,361,469 B2
(45) Date of Patent: Apr. 22, 2008

(54) DUAL LABELED FLUORESCENT PROBES

(75) Inventors: Joseph A. Sorge, Del Mar, CA (US);
Reinhold Mueller, San Diego, CA
(US); Gothami Padmabandu, San
Diego, CA (US)

(73) Assignee: Stratagene California, La Jolla, CA
(US)

( * ) Notice: Subject to any disclaimer, the term of this patent is extended or adjusted under 35 U.S.C. 154(b) by 0 days.

(21) Appl. No.: 11/203,320

(22) Filed: Aug. 12, 2005

(65) Prior Publication Data

US 2006/0088856 A1 Apr. 27, 2006

Related U.S. Application Data

(60) Provisional application No. 60/601,575, filed on Aug. 13, 2004.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. None
See application file for complete search history.

(56) References Cited

U.S. PATENT DOCUMENTS

| 5,723,591 | A | 3/1998 | Livak et al. |
| 5,928,869 | A * | 7/1999 | Nadeau et al. .................. 435/6 |
| 6,037,130 | A | 3/2000 | Tyagi et al. |
| 6,150,097 | A | 11/2000 | Tyagi et al. |
| 6,174,670 | B1 | 1/2001 | Wittwer et al. |
| 6,277,607 | B1 | 8/2001 | Tyagi et al. |
| 7,195,871 | B2 * | 3/2007 | Lyamichev et al. ............ 435/6 |

OTHER PUBLICATIONS

Stratagene Catalog, p. 39 (1988).*

* cited by examiner

*Primary Examiner*—Teresa E. Strzelecka

(57) ABSTRACT

The present invention relates to probes useful for the detection and measurement of target nucleic acids, as well as compositions and kits containing such probes. The probes of the present invention include an interactive pair of labels, as well as a hairpin sequence that does not hybridize to a target nucleic acid. According to the present invention, the probe generates a detectable signal indicative of a presence of a target nucleic acid. The detectable signal emitted by one of the pair of labels is substantially constant upon binding of the probe to target nucleic acid, and the detectable signal increases by at least 2 fold upon cleavage of the probe between the pair of labels.

55 Claims, 14 Drawing Sheets

Figure 5.

```
      T  T
   T T
  T  G-C
     C-G
     G-C
5'-T-A   T
         T  T
            ACAGGCAGCCAGCTGTTCCTCCTT-3'-c3 FAM
            |
            BHQ-2
```

TNF-α Flap +2T FullVelocity Probe

Figure 9. 042204-TEST DIFFERENT TNF-α FLAP PROBES-.MXP RAW DATA

Standard Curve

*040504-FLAP probe std curve-FAST.mxp*

Figure 13.

Ct Table for TNF-α Flap Probes

| | FLAP | FLAP + 2T | FLAP -Shift | FLAP+2T shift | ABI / in TM |
|---|---|---|---|---|---|
| Ct 50ng gDNA | 23.2 | 23.7 | 23.0 | 23.2 | 24.1 |
| Ct / NTC | No Ct | No Ct | No Ct | No Ct | No Ct |

Figure 14.

TNF-α in Human gDNA Detected with a Flap-Probe in FullVelocity Reagents or with a Linear Hydrolysis Probe in ABI QPCR Master Mix

Regular Cycling

| Probe | Quantity (ng) | Ct (dRn) | Threshold (dRn) |
|---|---|---|---|
| Flap | 50 | 22.99 | 0.050 |
| Flap | 10 | 25.03 | 0.050 |
| Flap | 2 | 27.87 | 0.050 |
| Flap | 0 | No Ct | 0.050 |
| Linear | 50 | 24.12 | 0.050 |
| Linear | 10 | 26.34 | 0.050 |
| Linear | 2 | 29.17 | 0.050 |
| Linear | 0 | No Ct | 0.050 |

Fast Cycling

| Probe | Quantity (ng) | Ct (dRn) | Threshold (dRn) |
|---|---|---|---|
| Flap | 50 | 24.77 | 0.050 |
| Flap | 10 | 26.26 | 0.050 |
| Flap | 2 | 28.30 | 0.050 |
| Flap | 0 | No Ct | 0.050 |
| Linear | 50 | 26.69 | 0.050 |
| Linear | 10 | 28.58 | 0.050 |
| Linear | 2 | 31.22 | 0.050 |
| Linear | 0 | No Ct | 0.050 |

DUAL LABELED FLUORESCENT PROBES

RELATED APPLICATION

This application claims the priority of U.S. Provisional Patent Application No. 60/601,575, filed Aug. 13, 2004, the entirety of which is incorporated herein, including figures.

FIELD OF INVENTION

The invention relates in general to compositions for detecting or measuring a target nucleic acid sequence.

BACKGROUND OF THE INVENTION

Techniques for polynucleotide detection have found widespread use in basic research, diagnostics, and forensics. Polynucleotide detection can be accomplished by a number of methods. Most methods rely on the use of the polymerase chain reaction (PCR) to amplify the amount of target DNA.

The TaqMan™ assay is a homogenous assay for detecting polynucleotides (U.S. Pat. No. 5,723,591). In this assay, two PCR primers flank a central probe oligonucleotide. The probe oligonucleotide contains two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the novel wavelength increases.

Molecular beacons are an alternative to TaqMan (U.S. Pat. Nos. 6,277,607; 6,150,097; 6,037,130) for the detection of polynucleotides. Molecular beacons are oligonucleotide hairpins which undergo a conformational change upon binding to a perfectly matched template. The conformational change of the oligonucleotide increases the physical distance between a fluorophore moiety and a quencher moiety present on the oligonucleotide. This increase in physical distance causes the effect of the quencher to be diminished, thus increasing the signal derived from the fluorophore.

U.S. Pat. No. 6,174,670B1 discloses methods of monitoring hybridization during a polymerase chain reaction which are achieved with rapid thermal cycling and use of double stranded DNA dyes or specific hybridization probes in the presence of a fluorescence resonance energy transfer pair—fluorescein and Cy5.3 or Cy5.5. The method amplifies the target sequence by polymerase chain reaction in the presence of two nucleic acid probes that hybridize to adjacent regions of the target sequence, one of the probes being labeled with an acceptor fluorophore and the other probe labeled with a donor fluorophore of a fluorescence energy transfer pair such that upon hybridization of the two probes with the target sequence, the donor fluorophore interacts with the acceptor fluorophore to generate a detectable signal. The sample is then excited with light at a wavelength absorbed by the donor fluorophore and the fluorescent emission from the fluorescence energy transfer pair is detected for the determination of that target amount.

There are also several other fluorescent and enzymatic probes for polynucleotide detection, such as Scorpions™, Sunrise™ primers, and DNAzymes, where each polynucleotide to be detected requires a different oligonucleotide probe and two different fluorescent moieties. These probes are usually custom-synthesized and are thus expensive.

SUMMARY OF THE INVENTION

The present invention relates to probes useful for the detection and measurement of target nucleic acids. The probes of the present invention include an interactive pair of labels. According to the present invention, the probe generates a signal indicative of a presence of a target nucleic acid.

In one aspect, the invention provides for an oligonucleotide probe having a 5' and 3' end, comprising:
(a) a hairpin sequence that does not hybridize to a target nucleic acid and consisting of a stem and a loop;
(b) a target binding sequence that forms a hybrid with a target nucleic acid; and,
(c) an interactive pair of labels, consisting of a first and second member.

According to this aspect, the hairpin sequence and the target binding sequence are covalently linked. The first member of the pair is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In another aspect, the invention provides for an oligonucleotide probe having a 5' and 3' end, comprising:
(a) a hairpin sequence that does not hybridize to a target nucleic acid and consisting of a stem and a loop;
(b) a target binding sequence that forms a hybrid with a target nucleic acid; and,
(c) an interactive pair of labels, consisting of a first and second member.

According to this aspect, the hairpin sequence and the target binding sequence are covalently linked such that the hairpin sequence is positioned 5' of the target binding sequence. The first member of the pair is attached to the 3' terminus of the target binding sequence and the second member of the pair is attached to the oligonucleotide probe between the 3' terminus and the hairpin sequence. A detectable signal emitted by one of the pair of labels is substantially constant upon binding of the probe to target nucleic acid, and the detectable signal increases by at least 2 fold upon cleavage of the probe between the pair of labels.

In a third aspect, the invention provides for an oligonucleotide probe having a 5' and 3' end, comprising:
(a) a hairpin sequence that does not hybridize to a target nucleic acid and consisting of a stem and a loop;
(b) a target binding sequence that forms a hybrid with a target nucleic acid; and,
(c) an interactive pair of labels, consisting of a first and second member.

According to this third aspect, the hairpin sequence and the target binding sequence of the probe are covalently linked such that the hairpin sequence is positioned 3' of the target binding sequence. The first member of the pair of labels is attached to the 5' terminus of the target binding sequence and the second member of the pair is attached to the oligonucleotide probe between the 3' terminus of the target binding sequence and the hairpin sequence. A detectable signal emitted by one of the pair of labels is substantially constant upon binding of the probe to target nucleic acid, and the detectable signal increases by at least 2 fold upon cleavage of the probe between the pair of labels.

The probes described above can further comprise a linker sequence, located between the hairpin sequence and the target binding sequence. The linker sequence of the probe can comprise between 1 and 15 nucleotides. In one embodiment, the linker sequence comprises between 1 and 10 nucleotides. In another embodiment, the linker sequence comprises between 1 and 5 nucleotides.

In one embodiment of these aspects, one type of pair of interactive labels is a fluorophore quencher pair. The fluorophore can be selected from the group consisting of FAM, R110, TAMRA, R6G, CAL Fluor Red 610, CAL Fluor Gold 540, and CAL Fluor Orange 560. The quencher can be selected from the group consisting of dark quenchers, DABCYL, BHQ-1, BHQ-2, and BHQ-3.

The stem of the hairpin sequence of the probe can be between 2 to 20 base pairs. In one embodiment, the stem of the hairpin sequence is between 3 to 10 base pairs. In another embodiment, the stem of the hairpin sequence is between 4 to 8 base pairs.

The loop of the hairpin sequence can be between 2 and 30 bases. In one embodiment, the loop of the hairpin sequence is between 3 and 20 bases. In another embodiment, the loop of the hairpin sequence is between 3 and 10 bases.

One of the fluorophore or quencher is attached at the 3' nucleotide of the target binding sequence. In one embodiment, the fluorophore or quencher is attached at the —OH moiety of the 3' nucleotide of the sequence.

The other of the fluorophore or quencher can be attached to linker sequence. Alternatively, the fluorophore or quencher can be attached to the target binding sequence.

The fluorophore and quencher are separated from one another by between 5 and 60 nucleotides. In one embodiment, the fluorophore and the quencher are separated by between 10 and 30 nucleotides. In another embodiment, the fluorophore and the quencher are separated by between 14 and 22 nucleotides.

The fluorophore and quencher can be directly attached to a nucleotide on the probe. Alternatively, the fluorophore and quencher can be indirectly attached via a spacer.

The probe of the present invention can be attached to a solid support. In one embodiment, the solid support is attached to the 5' end of the hairpin sequence.

In another aspect, the invention provides for a method of detecting a target nucleic acid, by incubating an oligonucleotide probe under conditions which permit hybridization of the probe to target in a sample comprising a target nucleic acid with a nucleic acid polymerase and a FEN nuclease and cleaving the probe between a pair of interactive labels with a FEN nuclease to generate a signal. Generation of the signal is indicative of the presence of a target nucleic acid sequence in the sample. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In one embodiment, the nucleic acid polymerase substantially lacks 5' to 3' exonuclease activity. In another embodiment, the nucleic acid polymerase is a DNA polymerase. In yet another embodiment, the nucleic acid polymerase is thermostable.

In one embodiment, the FEN nuclease is thermostable.

In yet another aspect, the invention provides for a composition comprising an oligonucleotide probe and a primer. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In one embodiment, the composition further comprises a nucleic acid polymerase. The nucleic acid polymerase can be a DNA polymerase. In one embodiment, the nucleic acid polymerase substantially lacks 5' to 3' exonuclease activity.

In another embodiment, the composition further comprises a FEN nuclease.

In another aspect, the invention provides for a composition comprising an oligonucleotide probe and a nucleic acid polymerase. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

The nucleic acid polymerase can be a DNA polymerase. In one embodiment, the nucleic acid polymerase substantially lacks 5' to 3' exonuclease activity. In another embodiment, the composition further comprises a FEN nuclease.

In another embodiment, the composition further comprises a primer.

In yet another aspect, the invention provides for a kit for generating a signal indicative of the presence of a target nucleic acid sequence in a sample, comprising an oligonucleotide probe, a nucleic acid polymerase substantially lacking 5' to 3' exonuclease activity, and packaging material therefore. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In one embodiment, the kit further comprises a suitable buffer. The kit can further comprise a FEN nuclease. In another embodiment, the kit further comprises a primer.

In still another aspect, the invention provides for a kit for generating a signal indicative of the presence of a target nucleic acid sequence in a sample, comprising an oligonucleotide probe, a FEN nuclease, and packaging material therefore. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In one embodiment, the kit further comprises a suitable buffer. In another embodiment, the kit further comprises a nucleic acid polymerase substantially lacking 5' to 3' exonuclease activity. In yet another embodiment, the kit further comprises a primer.

In still another aspect, the invention provides for a kit for generating a signal indicative of the presence of a target nucleic acid sequence in a sample, comprising an oligonucleotide probe, a primer, and packaging material therefore. According to this aspect, the oligonucleotide probe has a 5' and 3' end, comprising:

(a) a hairpin sequence that does not hybridize to a target nucleic acid and consists of a stem and a loop;

(b) target binding sequence forms a hybrid with a target nucleic acid; and, (c) an interactive pair of labels, consisting of a first and second member.

According to this aspect, the hairpin sequence and the target binding sequence of the oligonucleotide probe are covalently linked. The first member of the pair of interactive labels is attached between the hairpin sequence and the target binding sequence and the second member of the pair is attached to the target binding sequence at the terminus distal to the hairpin sequence. A detectable signal emitted by one of the pair of labels is substantially constant upon binding of the probe to target nucleic acid, and the detectable signal increases by at least 2 fold upon cleavage of the probe between the pair of labels.

In one embodiment, the kit further comprises a suitable buffer. In another embodiment, the kit further comprises a nucleic acid polymerase substantially lacking 5' to 3' exonuclease activity. In yet another embodiment, the kit further comprises a FEN nuclease.

Further features and advantages of the invention will become more fully apparent in the following description of the embodiments and drawings thereof, and from the claims.

BRIEF DESCRIPTION OF FIGURES

FIG. 5 illustrates the TNF-a Flap +2T Full Velocity Probe. The probe sequence corresponds to SEQ ID NO: 3.

FIG. 13 shows the threshold cycle (Ct) values for the probes of FIGS. 4-7, and an ABI type probe.

FIG. 14 shows a comparison of the Ct values using a flap probe or an ABI type probe at various concentrations of target DNA, and in regular or fast cycling reactions.

DETAILED DESCRIPTION

Definitions

Figure 1:
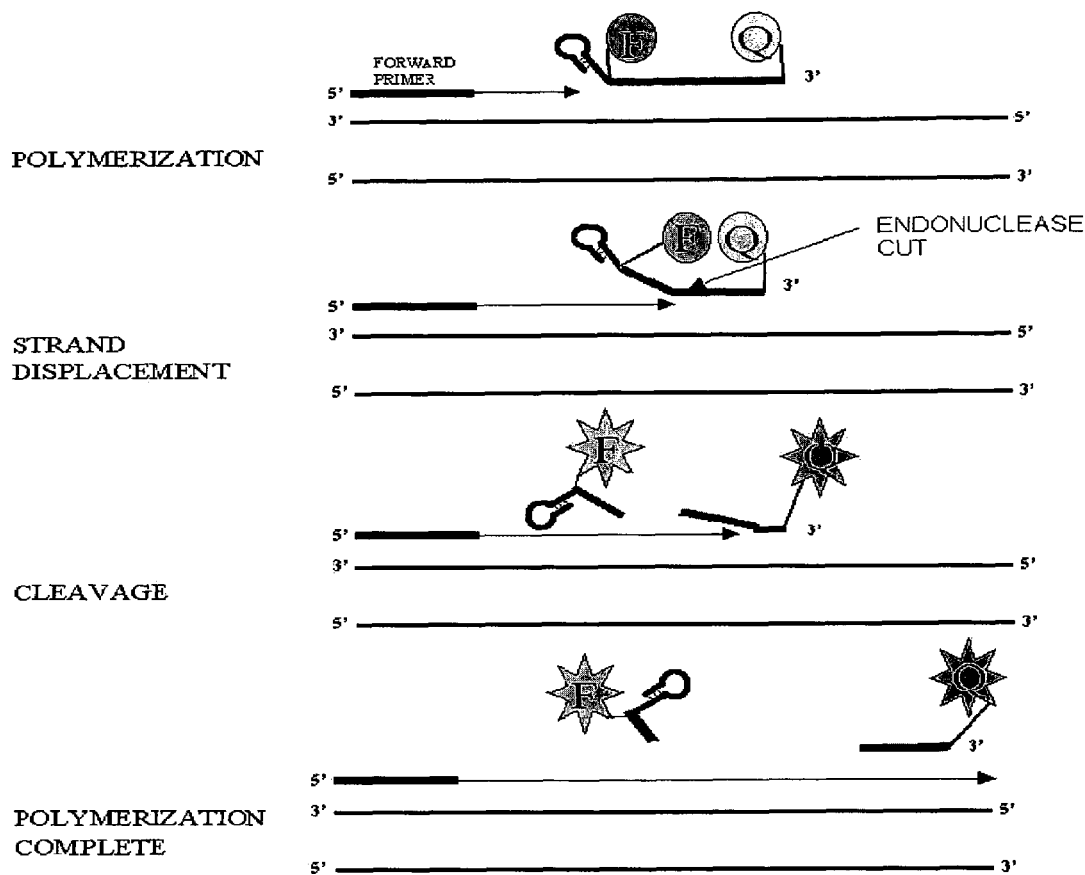
FIG. 1 illustrates a method for detecting the presence of a nucleic acid in a sample utilizing a probe that is degraded during an amplification reaction.

As used herein, a "target binding sequence" refers to a sequence which hybridizes to a target nucleic acid. As used herein, the terms "target polynucleotide" and "target nucleic acid" refer to a polynucleotide whose amount is to be determined in a sample. A "target nucleic acid" of the present invention contains a known sequence of at least 20 nucleotides, preferably at least 50 nucleotides, more preferably at least 100 or more nucleotides, for example, 500 or more nucleotides. A "target nucleic acid" of the invention may be a naturally occurring polynucleotide (i.e., one existing in nature without human intervention), or a recombinant polynucleotide (i.e., one existing only with human intervention), including but not limited to genomic DNA, cDNA, plasmid DNA, total RNA, mRNA, tRNA, rRNA. The target polynucleotide also includes amplified products of itself, for example, as in a polymerase chain reaction. According to the invention, a "target polynucleotide" or "target nucleic acid" may contain a modified nucleotide which include phosphorothioate, phosphite, ring atom modified derivatives, and the like.

As used herein, a "polynucleotide" refers to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The term "polynucleotide" includes, without limitation, single- and double-stranded polynucleotide. The term "polynucleotide" as it is employed herein embraces chemically, enzymatically or metabolically modified forms of polynucleotide. "Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'-ends.

As used herein, the term "oligonucleotide" refers to a short polynucleotide, typically less than or equal to 150 nucleotides long (e.g., between 5 and 150, preferably between 10 to 100, more preferably between 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

As used herein, a "primer" refers to a type of oligonucleotide having or containing the length limits of an "oligonucleotide" as defined above, and having or containing a sequence complementary to a target polynucleotide, which hybridizes to the target polynucleotide through base pairing so to initiate an elongation (extension) reaction to incorporate a nucleotide into the oligonucleotide primer. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer is preferably single-stranded for maximum efficiency in amplification. "Primers" useful in the present invention are generally between about 10 and 100 nucleotides in length, preferably between about 17 and 50 nucleotides in length, and most preferably between about 17 and 45 nucleotides in length. An "amplification primer" is a primer for amplification of a target sequence by primer extension. As no special sequences or structures are required to drive the amplification reaction, amplification primers for PCR may consist only of target binding sequences.

As used herein, a "probe" refers to a type of oligonucleotide having or containing a sequence which is complementary to another polynucleotide, e.g., a target polynucleotide or another oligonucleotide. The probe of the present invention is ideally less than or equal to 150 nucleotides in length, typically less than or equal to 100 nucleotides, for example less than or equal to 80, 70, 60 or 50 nucleotides in length.

As used herein, an "interactive pair of labels" and a "pair of interactive labels" refer to a pair of molecules which interact physically, optically or otherwise in such a manner as to permit detection of their proximity by means of a detectable signal. Examples of a "pair of interactive labels" include but are not limited to labels suitable for use in FRET (Stryer, L. Ann. Rev. Biochem. 47, 819-846, 1978), scintillation proximity assays ("SPA") (Hart and Greenwald, Molecular Immunology 16:265-267, 1979; U.S. Pat. No. 4,658,649), luminescence resonance energy transfer (LRET) (Mathis, G. Clin. Chem. 41, 1391-1397, 1995), direct quenching (Tyagi et al., Nature Biotechnology 16, 49-53, 1998), chemiluminescence energy transfer (CRET) (Campbell, A. K., and Patel, A. Biochem. J. 216, 185-194, 1983), bioluminescence resonance energy transfer (BRET) (Xu, Y., Piston D. W., Johnson, Proc. Natl. Acad. Sc., 96, 151-156, 1999), or excimer formation (Lakowicz, J. R. Principles of Fluorescence Spectroscopy, Kluwer Academic/Plenum Press, New York, 1999).

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer, photo induced electron transfer, paramagnetic enhancement of inter system crossing, Dexter exchange coupling, and exciton coupling such as the formation of dark complexes. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more.

As used herein, a detectable signal emitted by one of the pair of labels is "substantially constant", when the detectable signal emitted by the label changes 20% or less, for example, 20%, 19%, 15%, 10%, 5%, 2%, 1% or less.

An "increase in fluorescence", as used herein, refers to an increase in detectable fluorescence emitted by a fluorophore. An increase in fluorescence may result, for example, when the distance between a fluorophore and a quencher is increased, for example due to a cleavage reaction, such that the quenching is reduced. There is an "increase in fluorescence" when the fluorescence emitted by the fluorophore is increased by at least 2 fold, for example 2, 2.5, 3, 4, 5, 6, 7, 8, 10 fold or more.

As used herein, a "dark quencher" refers to a quencher moiety that absorbs energy from an excited fluorophore, but which does not release fluorescent energy itself. "Dark quenchers" useful in the present invention include, but are not limited to 4-(dimethylamino)azobenzene (DABCYL) and its derivatives, dinitrophenyl, DABMI, malachite green, QSY 7, QSY 9, QSY 21, QSY 35 ("QSY" quenchers available from Molecular Probes, Inc., Eugene, Oreg., see U.S. Pat. No. 6,329,205, incorporated herein by reference) and the black hole quenchers (BHQ) taught in WO01/86001.

As used herein, the term "complementary" refers to the concept of sequence complementary between regions of two polynucleotide strands or between two regions of the same polynucleotide strand. It is known that an adenine base of a first polynucleotide region is capable of forming specific hydrogen bonds ("base pairing") with a base of a second polynucleotide region which is anti parallel to the first region if the base is thymine or uracil. Similarly, it is known that a cytosine base of a first polynucleotide strand is capable of base pairing with a base of a second polynucleotide strand which is anti parallel to the first strand if the base is guanine. A first region of a polynucleotide is complementary to a second region of the same or a different polynucleotide if, when the two regions are arranged in an anti parallel fashion, at least one nucleotide of the first region is capable of base pairing with a base of the second region. Therefore, it is not required for two complementary polynucleotides to base pair at every nucleotide position. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 90%, or 80% or 70% complementary) contains mismatched nucleotides at one or more nucleotide positions. In one embodiment, two complementary polynucleotides are capable of hybridizing to each other under high stringency hybridization conditions. For example, for membrane hybridization (e.g., Northern hybridization), high stringency hybridization conditions are defined as incubation with a radio labeled probe in 5×SSC, 5×Denhardt's solution, 1% SDS at 65° C. Stringent washes for membrane hybridization are performed as follows: the membrane is washed at room temperature in 2×SSC/0.1% SDS and at 65° C. in 0.2×SSC/0.1% SDS, 10 minutes per wash, and exposed to film.

As used herein, a polynucleotide "isolated" from a sample is a naturally occurring polynucleotide sequence within that sample which has been removed from its normal cellular (e.g., chromosomal) environment. Thus, an "isolated" polynucleotide may be in a cell-free solution or placed in a different cellular environment.

As used herein, the term "amount" refers to an amount of a target polynucleotide in a sample, e.g., measured in μg, μmol or copy number. The abundance of a polynucleotide in the present invention is measured by the fluorescence intensity emitted by such polynucleotide, and compared with the fluorescence intensity emitted by a reference polynucleotide, i.e., a polynucleotide with a known amount.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. A "probe which shares no homology with another polynucleotide" refers to that the homology between the probe and the polynucleotide, as measured by BLASTN version 2.0 using the default parameters, is no more than 55%, e.g., less than 50%, or less than 45%, or less than 40%, or less than 35%, in a contiguous region of 20 nucleotides or more.

As used herein, references to "fluorescence" or "fluorescent groups" or "fluorophores" include luminescence and luminescent groups, respectively.

As used herein, a "spacer" refers to a chemical moiety comprising a covalent bond or a chain of atoms that covalently links or attaches a one moiety or molecule, for example the fluorophore or quencher, to the oligonucleotide.

As used herein, the term "hybridization" is used in reference to the pairing of complementary (including partially complementary) polynucleotide strands. Hybridization and the strength of hybridization (i.e., the strength of the association between polynucleotide strands) is impacted by many factors well known in the art including the degree of complementary between the polynucleotides, stringency of the conditions involved affected by such conditions as the concentration of salts, the melting temperature (Tm) of the formed hybrid, the presence of other components (e.g., the presence or absence of polyethylene glycol), the molarity of the hybridizing strands and the G:C content of the polynucleotide strands.

As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

As used herein, "5' to 3' exonuclease activity" or "5'→3' exonuclease activity" refer that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, Proc. Natl. Acad. Sci., USA, 65:168) fragment does not, (Klenow et al., 1971, Eur. J. Biochem., 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 μg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

Nucleic acid polymerases useful according to the invention substantially lack 5' to 3' exonuclease activity and include but are not limited to exo-Pfu DNA polymerase (a mutant form of Pfu DNA polymerase that substantially lacks 3' to 5' exonuclease activity, Cline et al., 1996, Nucleic Acids Research, 24: 3546; U.S. Pat. No. 5,556,772; commercially available from Stratagene, La Jolla, Calif. Catalogue # 600163), exo-Tma DNA polymerase (a mutant form of Tma DNA polymerase that substantially lacks 3' to 5' exonuclease activity), exo-Tli DNA polymerase (a mutant form of Tli DNA polymerase that substantially lacks 3' to 5' exonuclease activity New England Biolabs, (Cat #257)), exo-*E. coli* DNA polymerase (a mutant form of *E. coli* DNA polymerase that substantially lacks 3' to 5' exonuclease activity) exo-Klenow fragment of *E. coli* DNA polymerase I (Stratagene, Cat #600069), exo-T7 DNA polymerase (a mutant form of T7 DNA polymerase that substantially lacks 3' to 5' exonuclease activity), exo-KOD DNA polymerase (a mutant form of KOD DNA polymerase that substantially lacks 3' to 5' exonuclease activity), exo-JDF-3 DNA polymerase (a mutant form of JDF-3 DNA polymerase that substantially lacks 3' to 5' exonuclease activity), exo- PGB-D DNA polymerase (a mutant form of PGB-D DNA polymerase that substantially lacks 3' to 5' exonuclease activity) New England Biolabs, Cat. #259, Tth DNA polymerase, Taq DNA polymerase (e.g., Cat. Nos. 600131, 600132, 600139, Stratagene); UlTma (N-truncated) Thermatoga martima DNA polymerase; Klenow fragment of DNA polymerase I, $9^0$ Nm DNA polymerase (discontinued product from New England Biolabs, Beverly, Mass.), "3'-5' exo reduced" mutant (Southworth et al., 1996, Proc. Natl. Acad. Sci 93:5281) and Sequence (USB, Cleveland, Ohio). The polymerase activity of any of the above enzyme can be defined by means well known in the art. One unit of DNA polymerase activity, according to the subject invention, is defined as the amount of enzyme which catalyzes the incorporation of 10 nmoles of total dNTPs into polymeric form in 30 minutes at optimal temperature.

A "hairpin sequence", as used herein, comprises two self-complementary sequences that may form a double-stranded stem region, separated by a loop sequence. The two regions of the oligonucleotide which comprise the double-stranded stem region are substantially complementary to each other, resulting in self-hybridization. However, the stem can include one or more mismatches, insertions or deletions. The "hairpin sequence", as used herein, can additionally comprise single-stranded region(s) that extend from the double-stranded stem segment.

As used herein, when one polynucleotide is said to "hybridize" to another polynucleotide, it means that there is some complementary between the two polynucleotides or that the two polynucleotides form a hybrid under high stringency conditions. When one polynucleotide is said to not hybridize to another polynucleotide, it means that there is no sequence complementary between the two polynucleotides or that no hybrid forms between the two polynucleotides at a high stringency condition.

As used herein, "$T_m$" and "melting temperature" are interchangeable terms which are the temperature at which 50% of a population of double-stranded polynucleotide molecules becomes dissociated into single strands. The equation for calculating the Tm of polynucleotides is well known in the art. For example, the $T_m$ may be calculated by the following equation: $T_m=69.3+0.41\times(G+C)\%-650/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×4° C.], see, for example, C. R. Newton et al. PCR, $2^{nd}$ Ed., Springer-Verlag (New York: 1997), p. 24. Other more sophisticated computations exist in the art, which take structural as well as sequence characteristics into account for the calculation of $T_m$. A calculated $T_m$ is merely an estimate; the optimum temperature is commonly determined empirically.

"Primer extension reaction" or "chain elongation reaction" means a reaction between a target-primer hybrid and a nucleotide which results in the addition of the nucleotide to a 3'-end of the primer such that the incorporated nucleotide is complementary to the corresponding nucleotide of the target polynucleotide. Primer extension reagents typically include (i) a polymerase enzyme; (ii) a buffer; and (iii) one or more extendible nucleotides.

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule.

A "nucleotide analog", as used herein, refers to a nucleotide in which the pentose sugar and/or one or more of the phosphate esters is replaced with its respective analog. Exemplary pentose sugar analogs are those previously described in conjunction with nucleoside analogs. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage.

As used herein, the term "opposite orientation", when refers to primers, means that one primer (i.e., the reverse primer) comprises a nucleotide sequence complementary to the sense strand of a target nucleic acid template, and another primer (i.e., the forward primer) comprises a nucleotide sequence complementary to the antisense strand of the same target nucleic acid template. Primers with opposite orientations may generate a PCR amplified product from matched nucleic acid template to which they complement.

As used herein, the term "same orientation", means that both or all primers comprise nucleotide sequences complementary to the same strand of a target nucleic acid template. Primers with same orientation will not generate a PCR amplified product from matched nucleic acid template to which they complement.

As used herein a "nuclease" or a "cleavage agent" refers to an enzyme that is specific for, that is, cleaves a cleavage structure according to the invention and is not specific for, that is, does not substantially cleave either a probe or a primer that is not hybridized to a target nucleic acid, or a target nucleic acid that is not hybridized to a probe or a primer. The term "nuclease" includes an enzyme that possesses 5' endonucleolytic activity for example a DNA polymerase, e.g. DNA polymerase I from *E. coli*, and DNA polymerase from *Thermus aquaticus* (Taq), *Thermus thermophilus* (Tth), *Pyrococcus furiosus* (Pfu) and *Thermus flavus* (Tfl). The term nuclease also embodies FEN nucleases.

The term "FEN nuclease" encompasses any enzyme that possesses 5' exonuclease and/or an endonuclease activity. The term "FEN nuclease" also embodies a 5' flap-specific nuclease. A nuclease or cleavage agent according to the invention includes but is not limited to a FEN nuclease enzyme derived from *Archaeglobus fulgidus, Methanococcus jannaschii, Pyrococcus furiosus*, human, and mouse or *Xenopus laevis*. A nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli, Thermus aquaticus* (Taq), *Thermus flavus* (Tfl), *Bacillus caldotenax* (Bca), *Streptococcus pneumoniae*) and phage functional homologs of FEN including but not limited to T5 5' to 3' exonuclease, T7 gene 6 exonuclease and T3 gene 6 exonuclease. Preferably, only the 5' to 3' exonuclease domains of Taq, Tfl and Bca FEN nuclease are used. The term "nuclease" does not include RNAse H.

Description

The oligonucleotide probe of the present invention is used for monitoring or detecting the presence of target DNA in a nucleic acid amplification reaction. In one embodiment of such a nucleic acid amplification reaction, the oligonucleotide probe of the present invention is capable of hybridizing to the target DNA sequence at a location 3' relative to the location of hybridization of an amplification primer. In this method, nucleic acid amplification is performed on a target DNA sequence using a nucleic acid polymerase enzyme, for example, a thermostable DNA polymerase lacking exonuclease activity. As shown in FIG. 1, the newly synthesized nucleic acid strand displaces the oligonucleotide probe from the 5' end, leaving the probe in a conformation that renders it susceptible to nuclease cleavage. Cleavage of the oligonucleotide probe between a pair of interactive labels results in an enhanced detectable signal emitted by one member of the pair.

Without being bound to any one theory, it is believed that the probe retains its hairpin structure upon binding to the target sequence, and that the hairpin may thus play some role in retaining a constant position between the pair of interactive labels such that a detectable signal emitted by one member of the pair is substantially constant upon binding of the probe to the target.

The method according to the invention is performed using essentially reaction conditions for standard polymerase chain reaction (PCR), with the exception that two temperature cycles are performed: one, a high temperature denaturation step (generally between 90° C. and 96° C.) typically between 5 and 30 seconds, and a combined annealing/extension step (anywhere between 50° C. and 65° C., depending on the annealing temperature of the probe and primer), usually between 20 and 90 seconds. The reaction mixture contains a target nucleic acid, a nucleic acid polymerase as described above, the oligonucleotide probe of the present invention, suitable buffer and salts, and a FEN nuclease. The reaction can be performed in any thermocycler commonly used for PCR. However, preferred are cyclers with real-time fluorescence measurement capabilities, including instruments capable of measuring real-time including Taq Man 7700 AB (Applied Biosystems, Foster City, Calif.), Rotorgene 2000 (Corbett Research, Sydney, Australia), LightCycler (Roche Diagnostics Corp, Indianapolis, Ind.), iCycler (Biorad Laboratories, Hercules, Calif.) and Mx4000 (Stratagene, La Jolla, Calif.).

According to the present invention, the oligonucleotide probe can comprise natural, non-natural nucleotides and analogs. The probe may be a nucleic acid analog or chimera comprising nucleic acid and nucleic acid analog monomer units, such as 2-aminoethylglycine. For example, part or all of the probe may be PNA or a PNA/DNA chimera.

The probe of the present invention is ideally less than 150 nucleotides in length, typically less than 100 nucleotides, for example less than 80, 70, 60 or 50 nucleotides in length.

Use of a labeled probe generally in conjunction with the amplification of a target polynucleotide, for example, by PCR, e.g., is described in many references, such as Innis et al., editors, PCR Protocols (Academic Press, New York, 1989); Sambrook et al., Molecular Cloning, Second Edition (Cold Spring Harbor Laboratory, New York, 1989), all of which are hereby incorporated herein by reference. The binding site of the oligonucleotide probe is located between the PCR primers used to amplify the target polynucleotide. Preferably, PCR is carried out using Taq DNA polymerase, e.g., Amplitaq (Perkin-Elmer, Norwalk, Conn.), or an equivalent thermostable DNA polymerase, and the annealing temperature of the PCR is about 5° C.-10° C. below the melting temperature of the oligonucleotide probes employed.

Hairpin

The probe according to the present invention comprises a hairpin sequence. The hairpin sequence is located at 5' end of the target binding sequence, optionally separated by a linker sequence. The stem region of the hairpin can be between 2 to 20 base pairs, typically between 3 to 10 base pairs or between 3 and 8 base pairs.

The sequence of the hairpin structure is designed such that hybridization to target DNA is avoided. Therefore, the sequence of the hairpin sequence shares no homology with the target DNA. In addition, the stem structure is designed such that hybridization to regions of the probe outside of the stem forming regions is avoided. Therefore, the sequence of the stem regions shares no homology to other parts of the probe.

Hairpin sequences, like any other double-stranded nucleic acids, are subject to denaturation at appropriate conditions, including high temperatures, reduced ionic concentrations and/or the presence of disruptive chemical agents such as formamide or DMSO. The probes of the present invention preferably form hairpin sequences at the annealing/extension temperature, which is typically between 55-65° C. Therefore, hairpin sequences with a $T_m$ higher than the annealing/extension temperature are preferred, and can have a $T_m \geq 55°$ C., typically with a $T_m \geq 60°$ C., $Tm \geq 62°$ C., or $T_m \geq 65°$ C., can be used. The stability and melting temperature of hairpin sequences can be determined, for example, using programs such as mfold (Zuker (1989) Science, 244, 48-52) or Oligo 5.0 (Rychlik & Rhoads (1989) Nucleic Acids Res. 17, 8543-51). The appropriate sequence and length of the stem are chosen which have an ideal $T_m$ (e.g., >60° C.) and share no homology either with the target DNA or regions of the probe outside of the stem-forming regions.

The single-stranded loop sequence intervening the two stem-forming regions can vary in length between 1 to 40 bases, typically 2 to 30 bases, 3 to 20 bases, 4 to 15 bases, or 4 to 10 bases. The sequence of the loop can be any sequence, but should share no homology with the target DNA sequence, and should ideally share no homology with other regions of the probe. Example loop sequences include, but are not limited to, $A_n$ or $T_n$, where n is an integer between 3-6.

In an alternative embodiment, the hairpin sequence is located at the 3' end of the target binding sequence, optionally separated by a linker sequence. As is the case when attached at the 5' end of the target sequence, the stem region of the hairpin can be between 2 to 20 base pairs, typically between 3 to 10 base pairs or between 3 and 8 base pairs.

Linker Sequence

The probe according to the present invention can further comprise a linker sequence, placed between the hairpin sequence and the target binding sequence. A linker can be useful, for example, to ensure that the hairpin sequence forms without interfering with target binding sequence hybridizing to the target DNA, or to allow attachment of labels without interfering with hybridization of the target binding sequence to the target DNA. The linker sequence can comprise between 1 and 40 bases, typically between 1 and 25, between 1 and 20, between 1 and 15, between 1 and 10 and between 1 and 5 bases. There is no strict requirement regarding the linker sequence, so long as the linker sequence does not interfere with the formation of hairpin loop structure, or hybridizes to undesirable target.

Target Binding Sequence

The oligonucleotide probe of the present invention can be used as a hybridization probe to detect or measure target DNA in a sample. The oligonucleotide hybridizes to the target DNA with the target binding sequence. Accordingly, the target binding sequence is an oligonucleotide sequence which is complementary to the target DNA sequence. The region of the target DNA which is complementary to the target binding sequence is ideally located within 200 nucleotides downstream of (i.e., to the 3' of) the primer binding site, typically within 150, 125, or 100 nucleotides.

The ideal $T_m$ of target binding sequence is between 40° C. and 75° C., typically between 45° C. and 70° C., for example, between 50° C. and 65° C. As stated previously, the $T_m$ of the target binding sequence to the target DNA should ideally not exceed the $T_m$ of the hairpin sequence.

Fluorophore

A pair of interactive labels useful for the invention can comprise a pair of FRET-compatible dyes, or a quencher-dye pair. In one embodiment, the pair comprises a fluorophore-quencher pair.

Oligonucleotide probes of the present invention permit monitoring of amplification reactions by fluorescence. They can be labeled with a fluorophore and quencher in such a manner that the fluorescence emitted by the fluorophore in intact probes is substantially quenched, whereas the fluorescence in cleaved probes are not quenched, resulting in an increase in overall fluorescence upon probe cleavage. Furthermore, the generation of a fluorescent signal during real-time detection of the amplification products allows accurate quantitation of the initial number of target sequences in a sample.

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro -Fluorescein ([4,7,2',4',5',7'-hexachloro-(3',6'-dipivaloyl-fluoresceinyl)-6-carboxylic acid ]); 6-Hexachloro-Fluorescein ([4,7,2',4',5',7'-hexachloro-(3',6'-dipivaloylfluoresceinyl) -5- acid ]); 5-Tetrachloro-Fluorescein ([4,7,2',7'-tetra -chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethylamino); 6-TAMRA (6-carboxytetramethylrhodamine; Xanthylium, 9-(2,5-dicarboxyphenyl) -3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine -5) Cy3 (Indo-dicarbocyanine-3); and BODIPY FL (2,6-dibromo-4,4-difluoro-5,7-dimethyl-4-bora -3a, 4a- diaza -s-indacene -3-proprionic acid), Rox, as well as suitable derivatives thereof.

Quencher

The quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993, Proc. Natl. Acad. Sci., 90:2994-2998); Wu et al. (1994, Anal. Biochem., 218:1-13); Pesce et al., editors, *Fluorescence Spectroscopy* (1971, Marcel Dekker, New York); White et al., *Fluorescence Analysis: A Practical Approach* (1970, Marcel Dekker, New York); and the like. The literature also includes references providing exhaustive lists of fluorescent and chromogenic molecules and their relevant optical properties for choosing reporter-quencher pairs, e.g., Berlman, *Handbook of Fluorescence Spectra of Aromatic Molecules,* 2nd Edition (1971, Academic Press, New York); Griffiths, *Colour and Constitution of Organic Molecules* (1976, Academic Press, New York); Bishop, editor, *Indicators* (1972, Pergamon Press, Oxford); Haugland, *Handbook of Fluorescent Probes and Research Chemicals* (1992 Molecular Probes, Eugene) Pringsheim, *Fluorescence and Phosphorescence* (1949, Interscience Publishers, New York), all of which incorporated hereby by reference. Further, there is extensive guidance in the literature for derivatizing reporter and quencher molecules for covalent attachment via common reactive groups that can be added to an oligonucleotide, as exemplified by the following references, see, for example, Haugland (cited above); Ullman et al., U.S. Pat. No. 3,996, 345; Khanna et al., U.S. Pat. No. 4,351,760, all of which hereby incorporated by reference.

A number of commercially available quenchers are known in the art, and include but are not limited to DABCYL, BHQ-1, BHQ-2, and BHQ-3. The BHQ quenchers are a new class of dark quenchers that prevent fluorescence until a hybridization event occurs. In addition, these new quenchers have no native fluorescence, virtually eliminating background problems seen with other quenchers. BHQ quenchers can be used to quench almost all reporter dyes and are commercially available, for example, from Biosearch Technologies, Inc (Novato, Calif.).

Attachment of Fluorophore and Quencher

The probe according to the present invention has one of the fluorophore or quencher attached to the 3' nucleotide. Attachment of the fluorophore or quencher is preferably at the hydroxyl moiety of the 3' terminal nucleotide. Attachment can be made via direct coupling, or alternatively using a spacer molecule of between 1 and 5 atoms in length.

For the internal attachment of the fluorophore or quencher, linkage can be made using any of the means known in the art. Appropriate linking methodologies for attachment of many dyes to oligonucleotides are described in many references, e.g., Marshall, Histochemical J., 7: 299-303 (1975); Menchen et al., U.S. Pat. No. 5,188,934; Menchen et al., European Patent Application 87310256.0; and Bergot et al., International Application PCT/US90/ 05565. All are hereby incorporated by reference.

The other of the fluorophore or quencher can be attached anywhere within the probe outside the hairpin sequence, preferably at a distance from the other of the fluorophore/ quencher such that sufficient amount of quenching occurs. For example, if the fluorophore is attached to the 3' nucleotide of the probe, the quencher can be attached within the probe within either the target binding sequence or the optional linker sequence. Another preference is that the fluorophore and quencher be spaced sufficiently apart such that nuclease cleavage can occur readily between the two moieties during strand displacement. In one embodiment, the fluorophore and quencher are placed between 5 and 30 nucleotides of each other. In another embodiment, the fluorophore and quencher are placed between 10 and 25 nucleotides of each other. In still another embodiment, the fluorophore and quencher are placed between 14 and 21 nucleotides of each other.

When the oligonucleotide probe is intact, the moieties of the fluorophore/quencher pair are in a close, quenching relationship. For maximal quenching, the two moieties are ideally close to each other. In one embodiment, the quencher and fluorophore pair is positioned 22 bases or less from each other. In another embodiment, the pair is 18 bases or less. In yet another embodiment, the pair is positioned 15 bases or less from each other.

Attachment of Probes to a Solid Support

The probes of the present invention may also be linked to a solid support either directly, or through a chemical spacer. A solid support useful according to the invention includes but is not limited to silica-based matrices, cellulosic materials, plastic materials, membrane-based matrices and beads comprising surfaces including, but not limited to styrene, latex or silica based materials and other polymers. Magnetic beads are also useful according to the invention. Solid supports can be obtained commercially from several manufacturers.

It is well known by those with skill in the art that oligonucleotides can be synthesized with certain chemical and/or capture moieties, such that they can be coupled to solid supports. Examples of attaching oligonucleotides to solid supports can be found, for example, in U.S. Patent Application No. U.S. 2003/0165912 A1, which is hereby incorporated herein in its entirety. Suitable capture moieties include, but are not limited to, biotin, a hapten, a protein, a nucleotide sequence, an antigenic moiety, or a chemically reactive moiety. Such oligonucleotides may either be used first in solution and then captured onto a solid support, or first attached to a solid support and then used in a detection reaction.

An example of the latter would be to couple a probe to a solid support. The same probe would also comprise a fluorophore and quencher such that nuclease cleavage would physically liberate the quencher from the fluorophore, the latter of which remains on solid support after hydrolysis. For example, the target nucleic acid could hybridize with the solid-phase probe, and a liquid phase primer could also hybridize with the target molecule upstream of the probe binding site, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different probe molecules could be bound to different locations on an array. The location on the array would identify the probe molecule, and indicate the presence of the template to which the probe molecule can hybridize.

The methods of the invention can also be used in non-PCR based applications to detect a target nucleic acid sequence, where such target that may be immobilized on a solid support. Methods of immobilizing a nucleic acid sequence on a solid support are known in the art and are described in Ausubel FM et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc.

The probe of the present invention may be joined directly to the nucleotide or the primer, or it may be joined through a spacer. The spacer is preferably at least 30 atoms in length, typically at least 40, 50 or 60 atoms or more. Examples of suitable spacers are described in U.S. Pat. No. 5,770,716, which is hereby incorporated herein by reference.

The present invention is described by reference to the following Examples, which are offered by way of illustration and are not intended to limit the invention in any manner. Standard techniques well known in the art or the techniques specifically described below were utilized. All references cited herein are incorporated by reference.

EXAMPLES

Example 1

Probe Design

Figure 2:
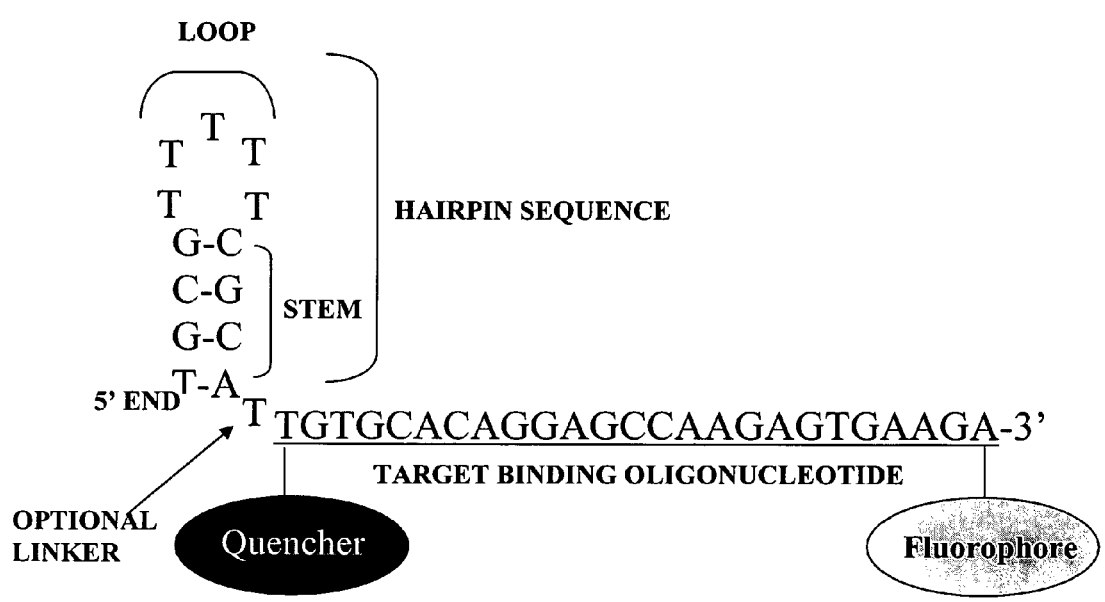
FIG. 2 illustrates one possible probe configuration. The probe sequence corresponds to SEQ ID NO: 1.
Figure 3:
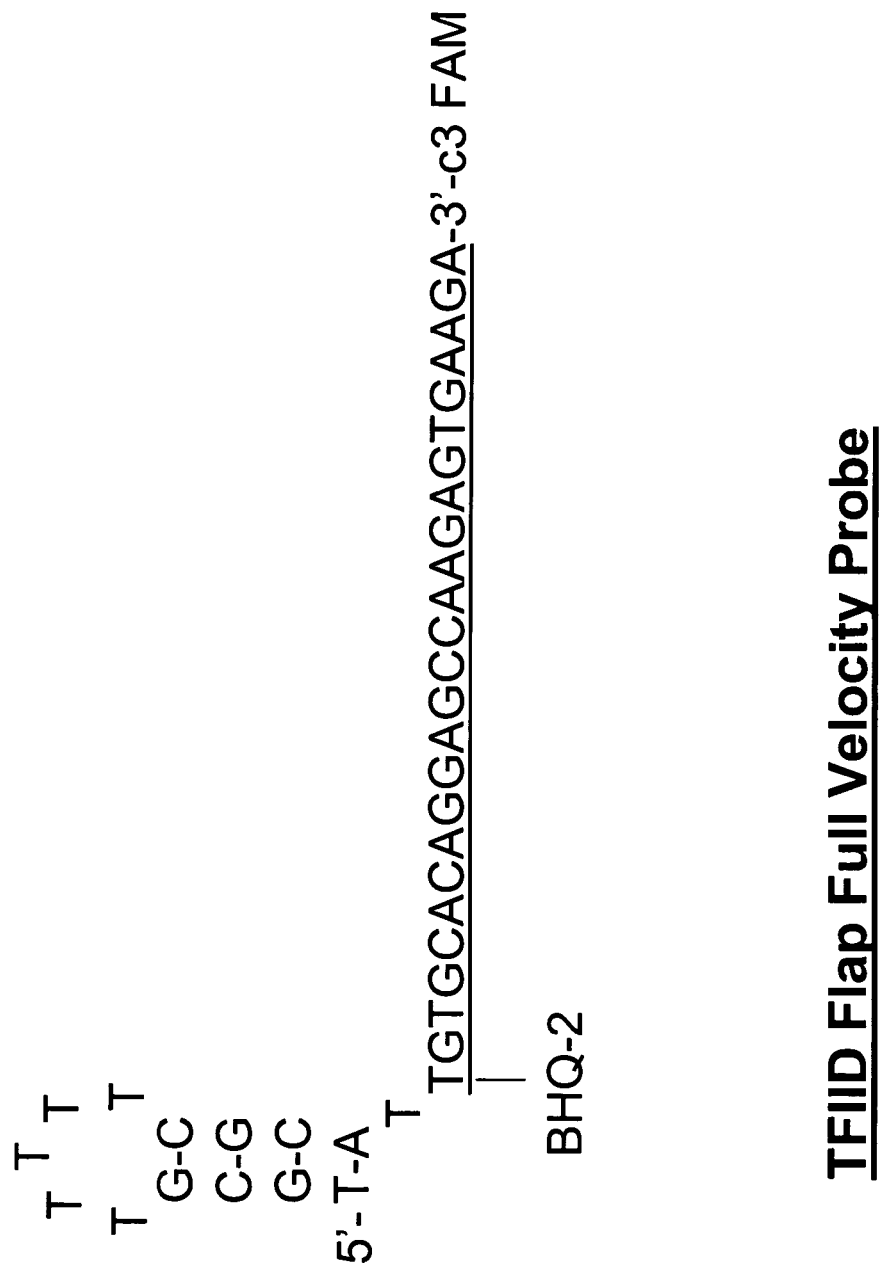
FIG. 3 illustrates the TFIID Flap Full Velocity Probe. The probe sequence corresponds to SEQ ID NO: 1.
Figure 4:
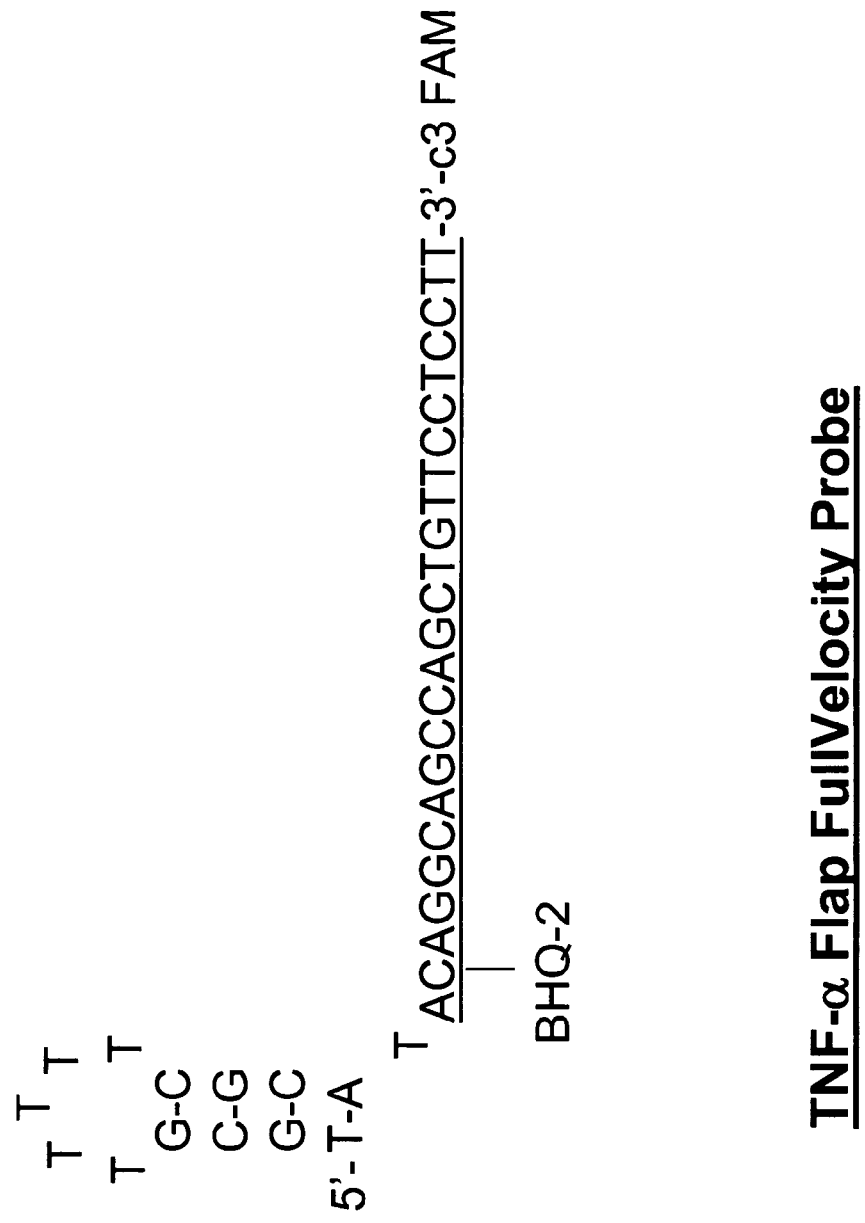
FIG. 4 illustrates the TNF-a Flap Full Velocity Probe. The probe sequence corresponds to SEQ ID NO: 2.
Figure 6:
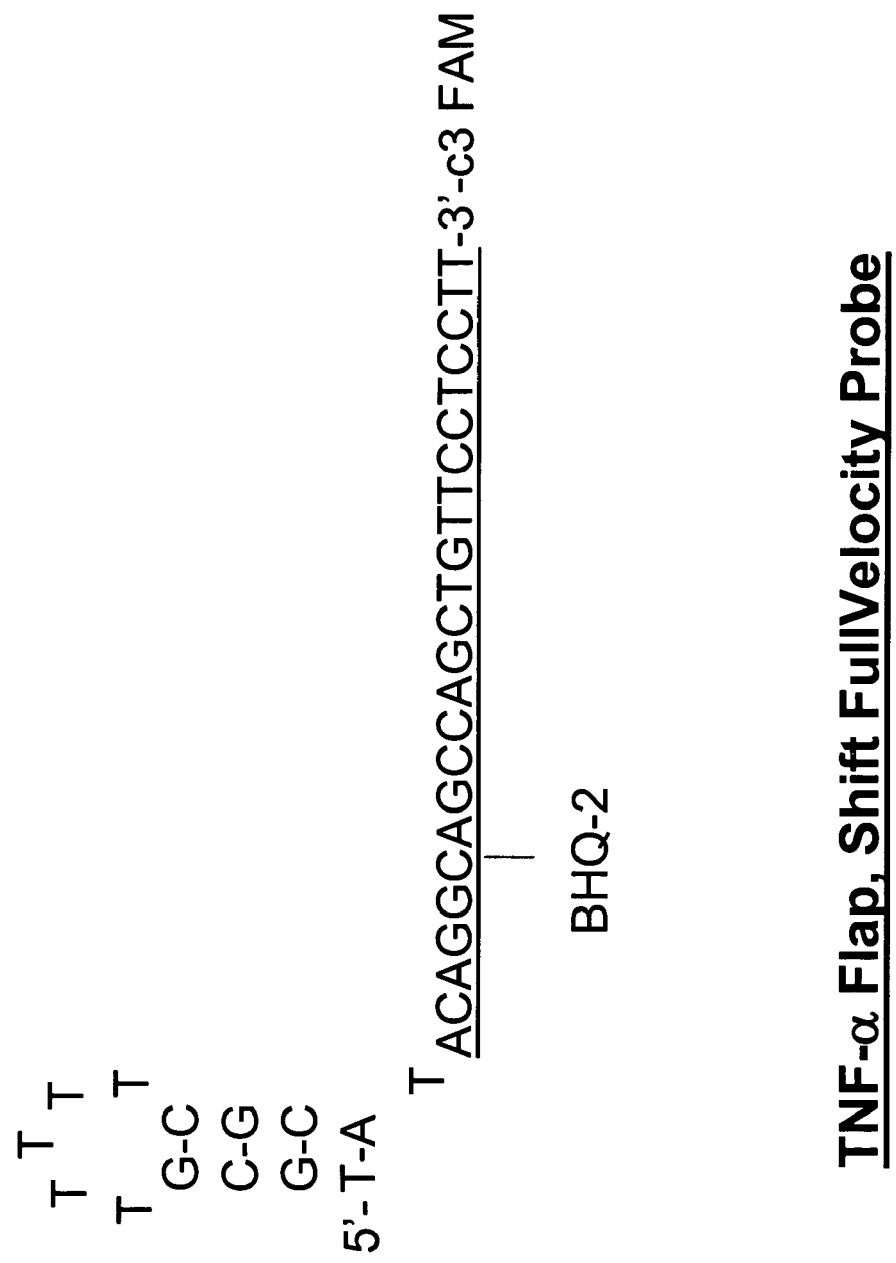
FIG. 6 illustrates the TNF-a Flap, Shift Full Velocity Probe. The probe sequence corresponds to SEQ ID NO: 2.
Figure 7:
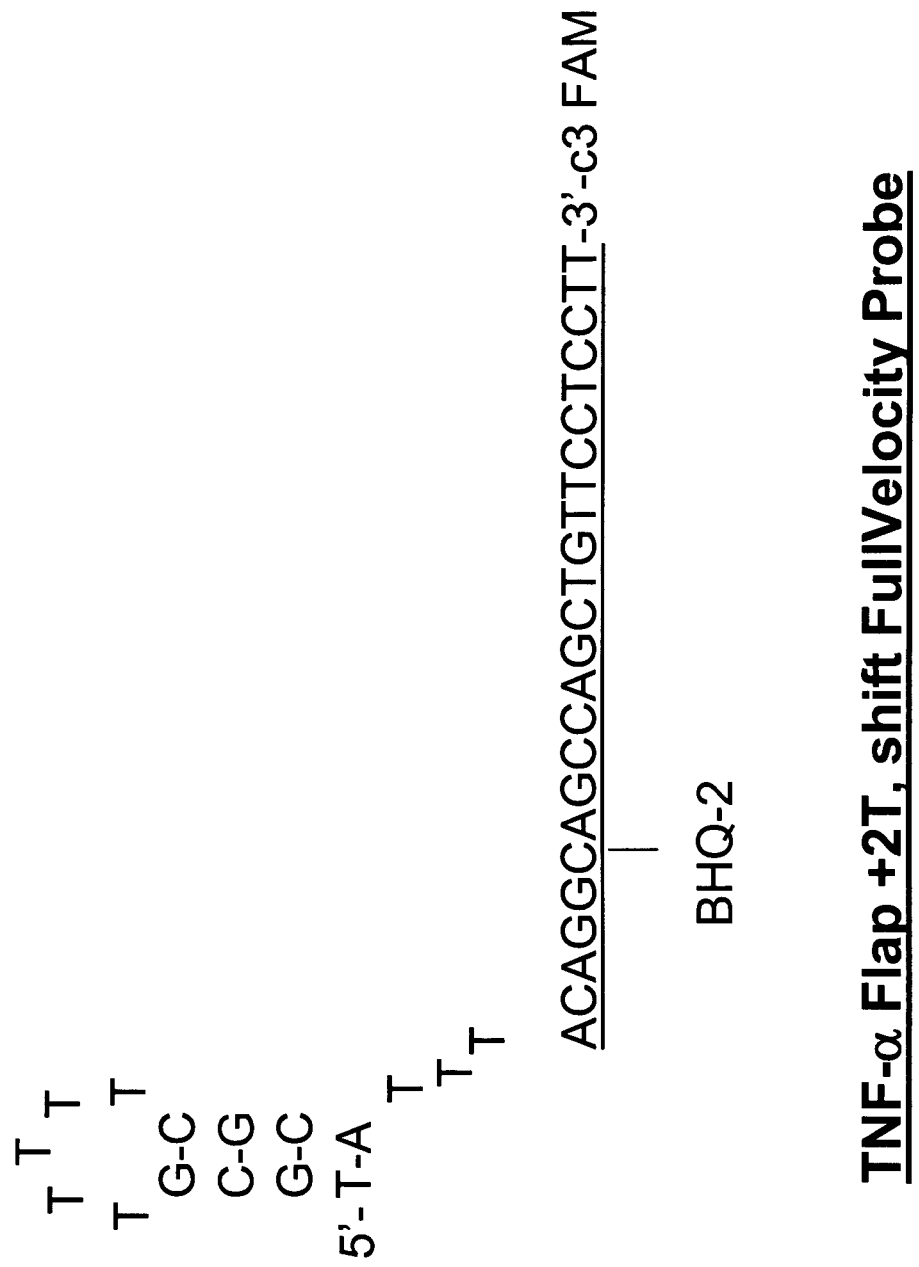
FIG. 7 illustrates the TNF-a Flap +2T, shift FullVelocity Probe. The probe sequence corresponds to SEQ ID NO: 3.

Probes, also called "flap probes", were designed according to embodiments of this invention. The first probe targeted the mouse TIMID mRNA (FIG. 2). The quencher, BHQ-2, is attached to the first T-residue of the DNA-binding domain. The dye, FAM is located at the 3'-end of the probe. The flap has a one-T-linker and a stem-loop structure with a $T_m > 60°$ C. Therefore, in a typical 2-step PCR, the stem is expected to be closed at the annealing/extension temperature, and to open up during the ramp to the melting plateau.

FIGS. 3 to 6 show four additional probes, targeting the human TNF-α gene. All four probes have a 3'-OH FAM label. The difference is that the internal quencher BHQ-2 is shifted by 4 nucleotides in 2 of the probes, and that two T's were added to the spacer of two of the probes. Fifty nanograms (ng) of human genomic DNA (gDNA) in 25 µl, including the passive reference dye, the primers and probes, were added to 25 µl of FullVelocity qPCR Kit (Stratagene, La Jolla, Calif., Catalog # 600561) 2×Master Mix, 300 nM of primers, and 300 nM of probe. Amplification was performed according to the manufacturer's conditions using the Mx 3000P real-time PCR system (Stratagene, La Jolla, Calif.). The samples were cycled with the following (regular cycling) program:

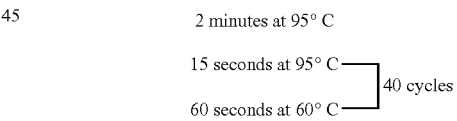

Figure 8:
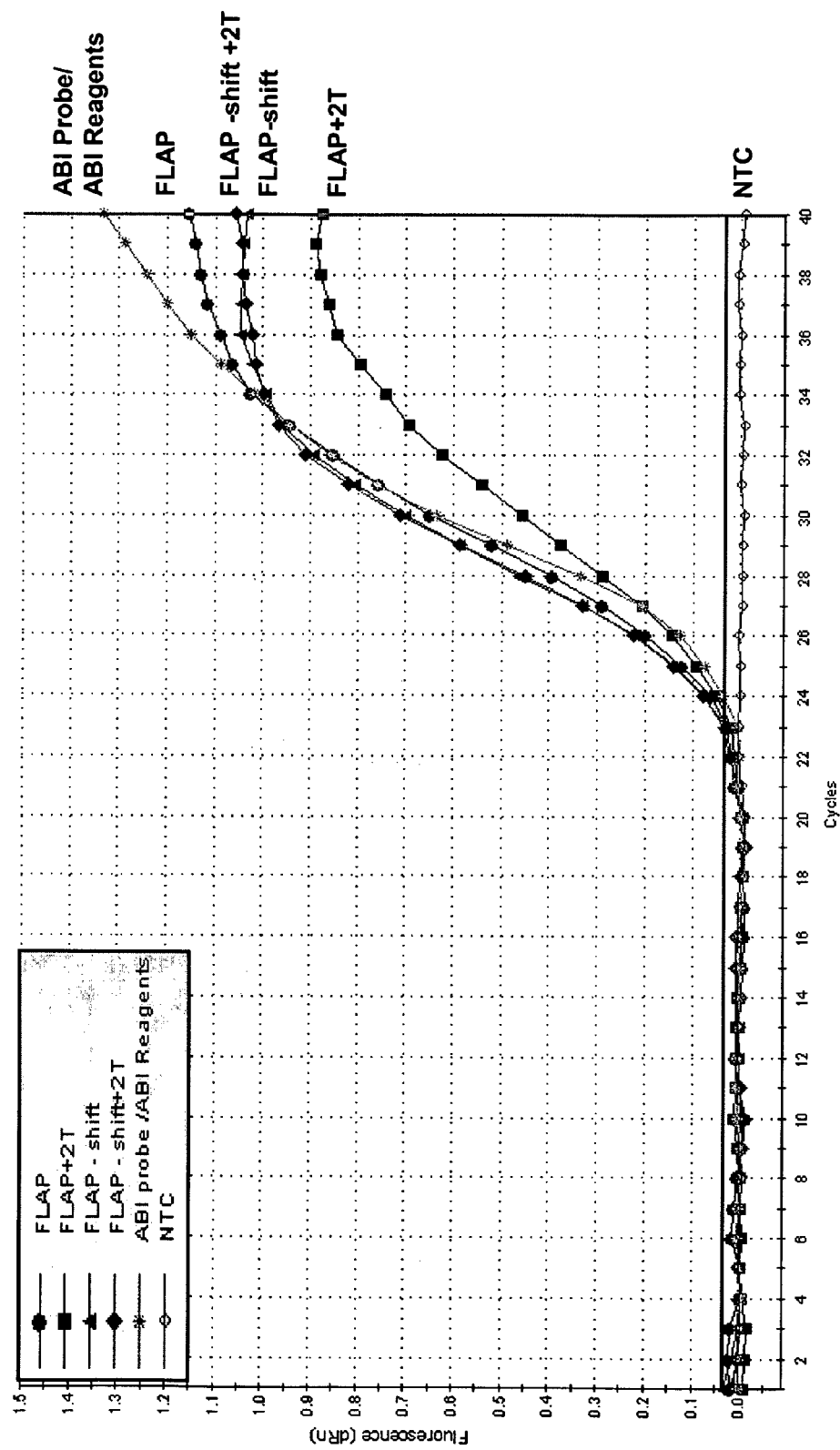
FIG. 8 shows the amplification plot showing the fluorescence values during amplification of the TNF-α gene using the probes of FIGS. 3-7, compared with an ABI type probe.
Figure 9:
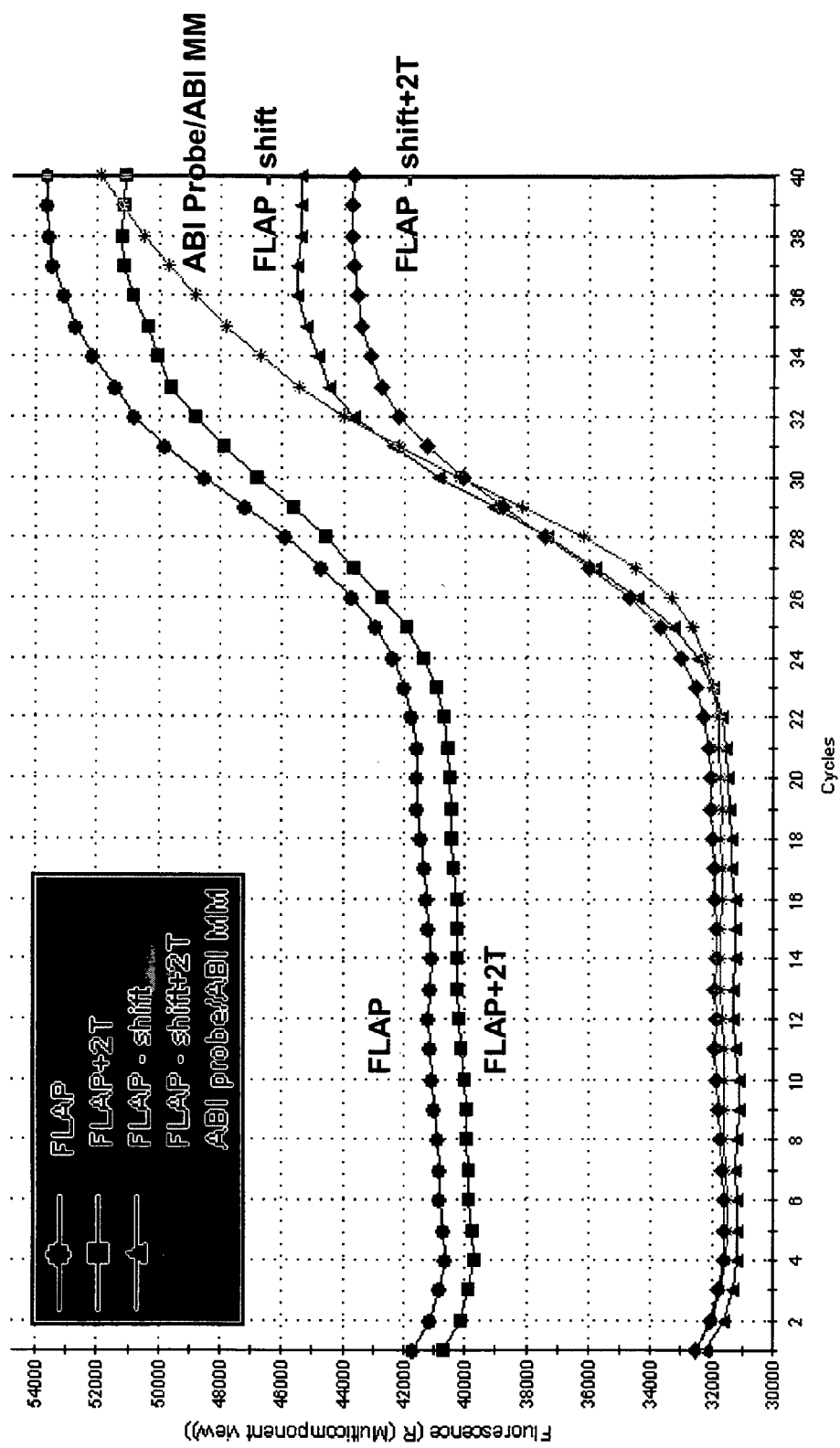
FIG. 9 shows the raw fluorescence data during amplification of the TNF-α gene using the probes illustrated in FIGS. 3-7.

Data acquisition was performed at the annealing/extension step. The averages of duplicate reactions are presented. The amplification plot is shown in FIG. 8 and the resulting threshold values are compiled in FIG. 13. The results indicate that the TNF-α flap probes have threshold cycles (Ct's) that are very close to each other; the Flap+2T probe (FIG. 5) has a slightly higher Ct than the Flap-shift probe (FIG. 6), which is 0.7 cycles faster (23.7 vs. 23.0, FIG. 13). A lower Ct translates into higher initial target concentration and in general, a difference of 3.4 cycles equals to a 10-fold difference in initial target concentration. The ABI-type probe, a linear oligonucleotide labeled with a 5'-FAM and a 3'-dark quencher/minor groove binder (MGB), has a Ct that is 1.1 higher than that for the Flap-shift probe (24.1 vs. 23.0, FIG. 13), although the target-binding domain is identical for the two probe types. The ABI type probe reactions were performed in the qPCR Master Mix from Applied Biosystems (Foster City, Calif., Cat# 4324018) using conditions suggested by the manufacturer. The amplification of the human TNF-α gene, detected with the same set of probes was analyzed using the Mx3000P raw data plot (FIG. 9). The results show that the initial fluorescence is higher for the Flap and Flap+2T probes (about 40,000 relative fluorescence units=RFU), compared to about 32,000 RFU for Flap-shift, Flap-shift+2T and ABI probes. This observation suggests that the distance between dye and quencher has a pronounced effect on the basal fluorescence of a probe. For a more stable signal, use of probes with a lower basal fluorescence and with a high signal-to-noise ratio is preferred.

Example 2

Performance of Flap and Linear Probes During Regular and Fast Cycling Protocols

In order to demonstrate the advantage of flap probes in FullVelocity reagents over linear hydrolysis probes qPCR using a common qPCR mixture, the cycling protocol was modified. The standard qPCR protocol (10 minutes at 95° C.; 40 times 15 seconds at 95° C./1 minute at 60° C.) takes approximately 90 minutes to complete. In contrast, the fast protocol (10 minutes at 95° C.; 40 times 10 seconds at 95° C./30 seconds at 60° C.) with flap probe and FullVelocity reagents can be completed in less than 55 minutes. Because the DNA polymerase in the ABI qPCR Master Mix requires 10 minutes of activation, the pre-melt plateau was extended from 2 minutes (as used in Example 1) to 10 minutes. The human TNF-α gene was the target for two detection systems. The first detection system included TNF-α PCR primers, the TNF-α flap probe (FIG. 4) and the FullVelocity qPCR Kit. The second detection system consisted of the same PCR primer set, a linear hydrolysis probe with identical DNA-binding sequence and the ABI qPCR Master Mix. Both detection systems (50 µl reactions in duplicate) were run on the Mx3000P using the regular cycling or the fast cycling protocol. For the analysis of the regular and the fast run the same threshold setting was chosen, which allows for comparison of the two runs. The averages of the replicate samples are shown in FIG. 14. In this experiment the Ct for the flap probe system is lower in both cycling protocols than for the conventional linear hydrolysis probe system, suggesting a gain in sensitivity of detecting TNF-α.

Example 3

Range of Linearity of the Flap Probes

Figure 10:
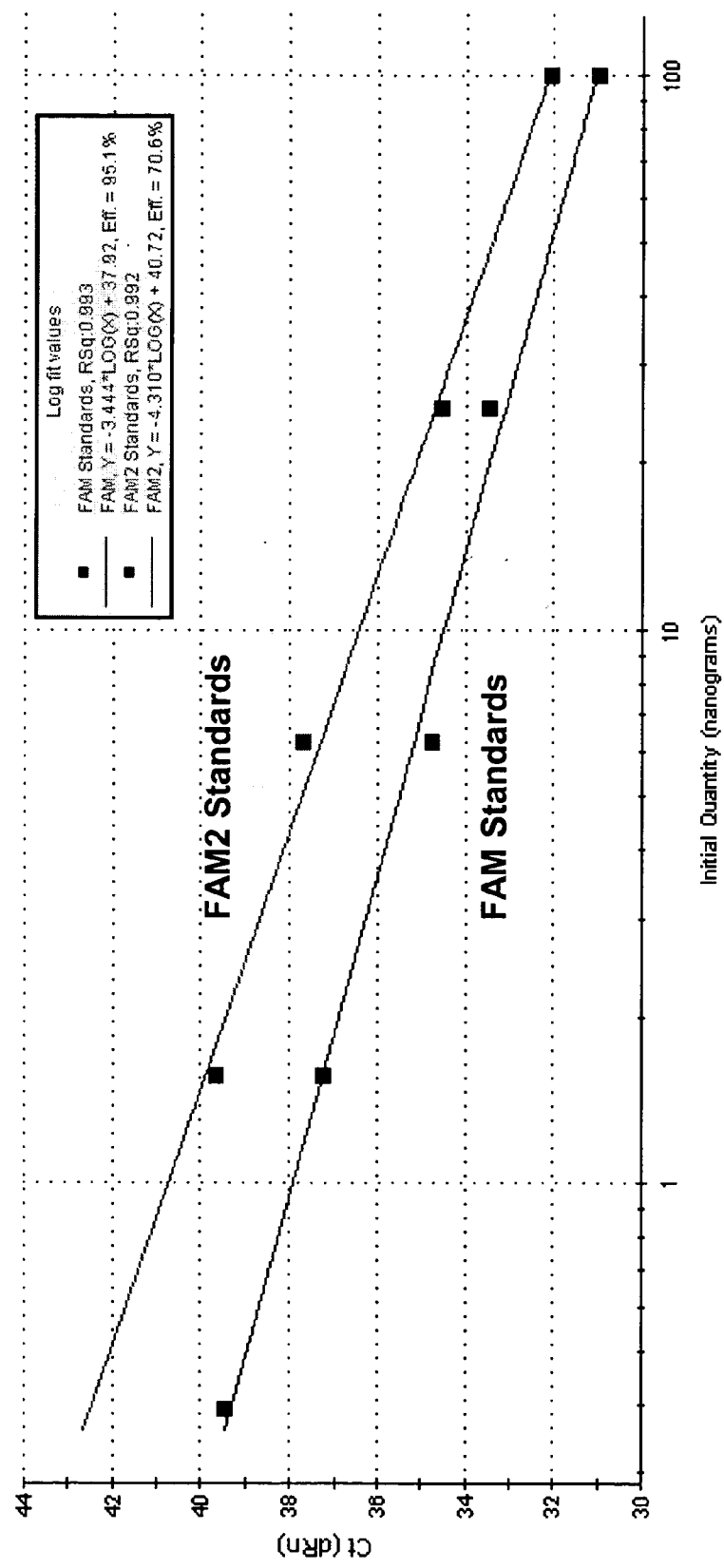
FIG. 10 shows standard curves generated by amplification of TIMID from cDNA generated from total mouse liver RNA. Probes used were the TIMID flap probe (FIG. 3) or an equivalent ABI type probe. Amplification was performed using fast conditions.

Mouse Liver Total RNA (Stratagene, Cat #736009) was reverse transcribed by using a First Strand Synthesis Kit (Stratagene, Cat # 200420) and random priming according to the manufacturer's conditions. The cDNA reactions were set up to contain 3.9, 15.6, 62.5, 250 or 1000 ng of RNA/50 µl. Five µl of cDNA (equivalent to 0.39 to 100 ng total RNA) was added to 45 µl duplicate reactions of FullVelocity qPCR reagents or to ABI qPCR Master Mix. The TIMID flap probe (300 nM) and primers (300 nM each) were included in the FullVelocity reagents. As a control the linear hydrolysis probe with identical DNA-binding sequence to the flap probe (300 nM) and primers (300 nM each) were included in the ABI Master Mix. After PCR in the Mx3000P using fast conditions (10 minutes at 95° C.; 40 times 10 seconds at 95° C./ 30 seconds at 60° C.) a standard curve was generated. FIG. 10 shows that both probe deliver a good curve fit [$r^2$=0.993 for the flap probe (bottom line) and $r^2$=0.992 for the linear hydrolysis probe (top line)]. The flap probe allows for the detection of 0.39 ng template, whereas the linear probe does not exhibit equivalent sensitivity of detection under fast conditions. Note that the ten minute initial denaturation/activation were performed at 95° C. to activate the chemically modified hot start enzyme in ABI Master Mix reactions.

Example 4

Amplification and Detection of RNA Targets Using Flap Probes

Figure 11:
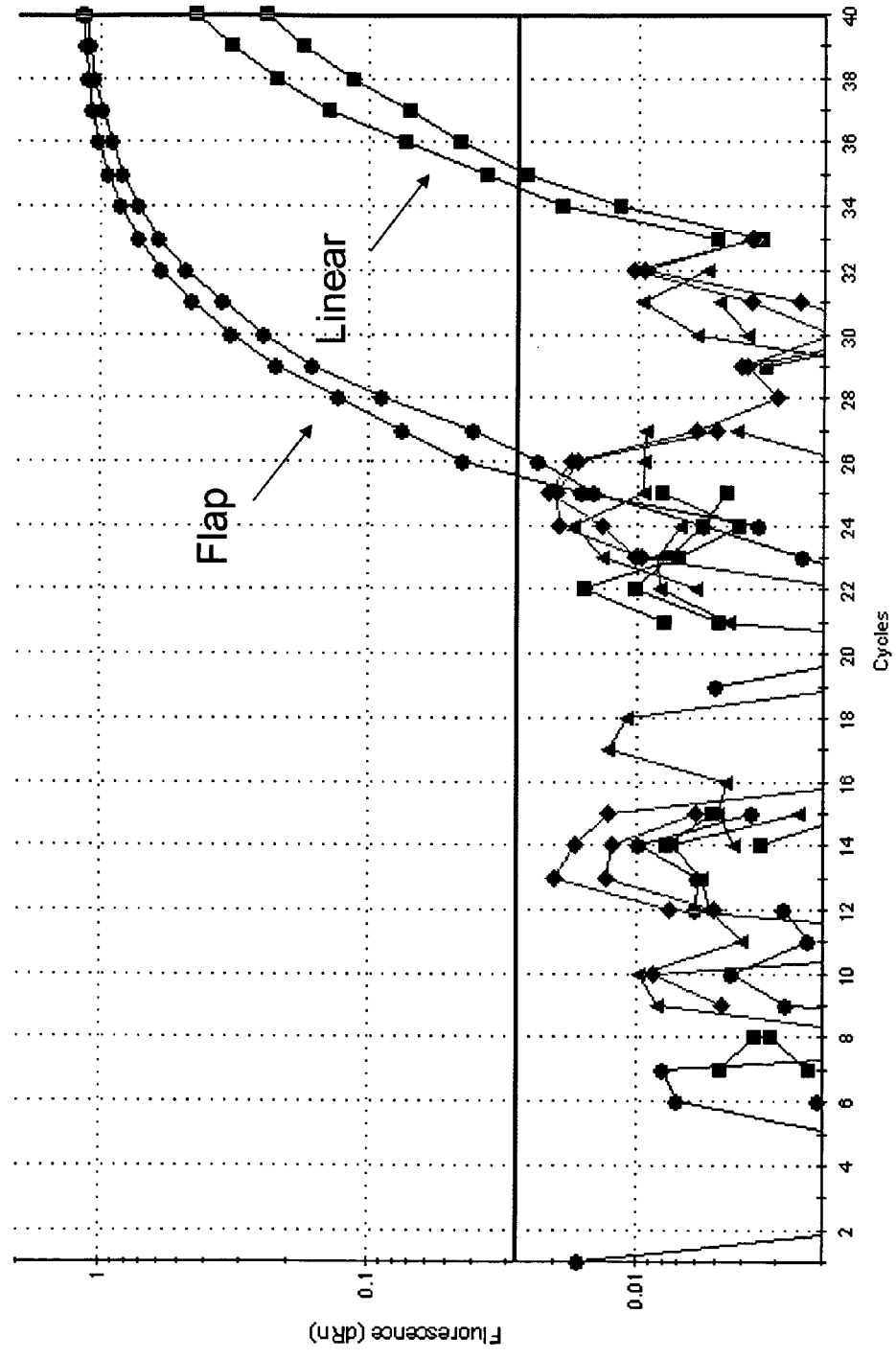
FIG. 11 shows detection of RNA templates in a single-tube qRT-PCR assay, using mouse liver total RNA using the TIMID flap probe (FIG. 3) or equivalent ABI type probe.

The utility of the flap probes in detecting RNA templates in a single-tube qRT-PCR assay is shown in FIG. 11. FullVelocity qRT-PCR reagents (Stratagene, Cat # 600562) were tested in 50 µl, duplicate reactions which contained 100 ng of mouse liver total RNA (Stratagene, Cat # 736009) and either TIMID primers and flap probe or ABI-type probe [a linear oligonucleotide labeled with a 5'-FAM and a 3'-dark quencher/minor groove binder (MGB)] with identical DNA-binding sequence to the flap probe. Amplification was performed in an Mx3000P with the following protocol: 15 minutes at 50° C., 5 minutes at 95° C.; 40 times 15 seconds at 95° C./1 minute at 60° C. The amplification plots shown in FIG. 11 indicate that the FullVelocity qRT-PCR kit supports the flap probe well (Ct of 26), while the ABI probe seems to perform sub-optimally (Ct of 35) in this FullVelocity qRT-PCR assay.

Example 5

Reproducibility of Amplification and Detection in Regular Cycling

Figure 12:
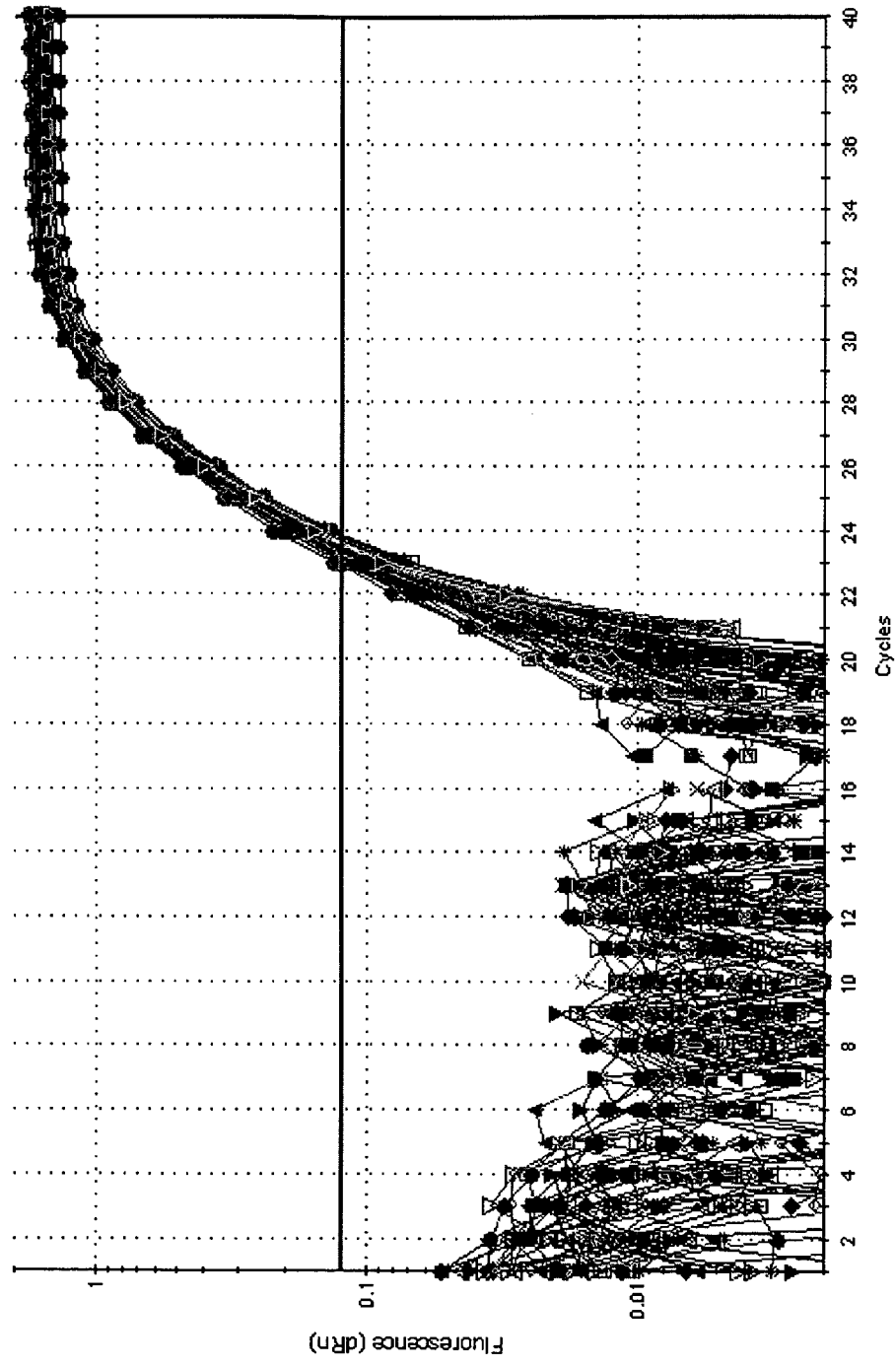
FIG. 12 shows the uniformity of amplification and detection using the TNF-α flap probe in a 96-well. Plot shows fluorescence values from each of the 96 wells, with the resulting Ct range of 0.82 for the 96 samples, with a coefficient of variation equaling 0.722%.

The TNF-α flap shift-probe (FIG. 6) was subjected to a 96-well uniformity assay. FullVelocity qPCR reagents including 100 ng human gDNA, flap probe (300 nM) and primers (300 nM each) were evenly distributed (25 µl each) into a 96-well plate and run in an Mx3000P under regular conditions. The resulting amplification plot is shown in FIG. 12. The analysis of the data showed that the Ct range for the 96 samples was 0.82 and the coefficient of variation (CV) equaled 0.722%, demonstrating excellent reproducibility.

The foregoing examples demonstrate experiments performed and contemplated by the present inventors in making and carrying out the invention. It is believed that these examples include a disclosure of techniques which serve to both apprise the art of the practice of the invention and to demonstrate its usefulness. Those of skill in the art will appreciate that the techniques and embodiments disclosed herein are preferred and non-limiting embodiments only, and that in general numerous equivalent methods and techniques may be employed to achieve the same result.

The invention claimed is:

1. An oligonucleotide probe having a 5' and 3' end, comprising:
   (a) a hairpin sequence that does not hybridize to a target nucleic acid and consisting of a stem and a loop;
   (b) a target binding sequence that forms a hybrid with a target nucleic acid; and,
   (c) an interactive pair of labels, consisting of a first and second member; wherein said hairpin sequence and said target binding sequence are covalently linked, wherein said first member of said pair is attached anywhere in said probe outside of said hairpin sequence and wherein said second member of said pair is attached to said target binding sequence at the terminus distal to said hairpin sequence, wherein a detectable signal is emitted by one of said pair of labels, and wherein said detectable signal increases by at least 2 fold upon cleavage of said probe between said pair.

2. The probe of claim 1, further comprising a linker sequence, located between said hairpin sequence and said target binding sequence.

3. The probe of claim 2, wherein said linker sequence comprises between 1 and 15 nucleotides.

4. The probe of claim 2, wherein said linker sequence comprises between 1 and 10 nucleotides.

5. The probe of claim 2, wherein said linker sequence comprises between 1 and 5 nucleotides.

6. The probe of claim 1, wherein said pair comprises a fluorophore and a quencher.

7. The probe of claim 6, wherein of one of said fluorophore or said quencher is attached to said 3' nucleotide such that said probe does not serve as a template for synthesis.

8. The probe of claim 7, wherein said fluorophore is attached to said 3' nucleotide.

9. The probe of claim 1, wherein said pair is separated by between 5 and 60 nucleotides.

10. The probe of claim 1, wherein said pair is separated by between 10 and 30 nucleotides.

11. The probe of claim 6, wherein said fluorophore is selected from the group consisting of FAM, R110, TAMRA, R6G, CAL Fluor Red 610, CAL Fluor Gold 540, and CAL Fluor Orange 560.

12. The probe of claim 6, wherein said quencher is selected from the group consisting of DABCYL, BHQ-1, BHQ-2, and BHQ-3.

13. The probe of claim 6, wherein said fluorescence increases upon cleavage of said probe between said fluorophore and quencher by at least 3 fold.

14. The probe of claim 6, wherein said fluorescence increases upon cleavage of said probe between said fluorophore and quencher by at least 4 fold.

15. The probe of claim 1, wherein said stem of said hairpin sequence is between 2 to 20 base pairs.

16. The probe of claim 1, wherein said stem of said hairpin sequence is between 3 to 10 base pairs.

17. The probe of claim 1, wherein said stem of said hairpin sequence is between 4 to 8 base pairs.

18. The probe of claim 1, wherein said loop of said hairpin sequence is between 2 and 30 bases.

19. The probe of claim 1, wherein said loop of said hairpin sequence is between 3 and 20 bases.

20. The probe of claim 1, wherein said loop of said hairpin sequence is between 3 and 10 bases.

21. The probe of claim 6, wherein one of said fluorophore or quencher is attached at the 3' OH moiety of said target binding sequence.

22. The probe of claim 6, wherein one of said fluorophore or quencher is attached to the linker sequence.

23. The probe of claim 6, wherein one of said fluorophore or quencher is attached to the target binding sequence.

24. The probe of claim 6, wherein said fluorophore or quencher is directly attached.

25. The probe of claim 6, wherein said fluorophore or quencher is indirectly attached via a spacer.

26. The probe of claim 6, further comprising a solid support.

27. The probe of claim 26, wherein said solid support is attached to the 5' end of said hairpin sequence.

28. An oligonucleotide probe having a 5' and 3' end, comprising:
   (a) a hairpin sequence that does not hybridize to a target nucleic acid and consisting of a stem and a loop;
   (b) a target binding sequence that forms a hybrid with a target nucleic acid; and,
   (c) an interactive pair of labels, consisting of a first and second member; wherein said hairpin sequence and said target binding sequence are covalently linked such that said hairpin sequence is positioned 5' of said target binding sequence, wherein said first member of said pair is attached to the 3' terminus of said target binding sequence and wherein said second member of said pair is attached to said oligonucleotide probe between said 3' terminus and said hairpin sequence, and wherein a detectable signal is emitted by one of said pair of labels, and wherein said signal increases by at least 2 fold upon cleavage of said probe between said pair.

29. An oligonucleotide probe having a 5' and 3' end, comprising:
   (a) a hairpin sequence that does not hybridize to a target nucleic acid and consisting of a stem and a loop;
   (b) a target binding sequence that forms a hybrid with a target nucleic acid; and,
   (c) an interactive pair of labels, consisting of a first and second member; wherein said hairpin sequence and said target binding sequence are covalently linked such that said hairpin sequence is positioned 3' of said target binding sequence; wherein said first member of said pair is attached to the 5' terminus of said target binding sequence and wherein said second member of said pair is attached to said oligonucleotide probe between the 3' terminus of said target binding sequence and said hairpin sequence; wherein a detectable signal is emitted by one of said pair of labels; and wherein said detectable signal increases by at least 2 fold upon cleavage of said probe between said pair.

30. A composition comprising the probe of claim 1 and a primer.

31. The composition of claim 30, further comprising a nucleic acid polymerase.

32. The composition of claim 31, wherein said nucleic acid polymerase is a DNA polymerase.

33. The composition of claim 31, wherein said nucleic acid polymerase substantially lacks 5' to 3' exonuclease activity.

34. The composition of claim 31, further comprising FEN nuclease.

35. A composition comprising the probe of claim 1, and a nucleic acid polymerase.

36. The composition of claim 35, wherein said nucleic acid polymerase substantially lacks 5' to 3' exonuclease activity.

37. The composition of claim 35, further comprising a FEN nuclease.

38. The composition of claim 35, further comprising a primer.

39. A kit for generating a signal indicative of the presence of a target nucleic acid sequence in a sample, comprising the probe of claim 1, a nucleic acid polymerase substantially lacking 5' to 3' exonuclease activity, and packaging material therefore.

40. The kit of claim 39, further comprising a suitable buffer.

41. The kit of claim 39, further comprising a FEN nuclease.

42. The kit of claim 39, further comprising a primer.

43. A kit for generating a signal indicative of the presence of a target nucleic acid sequence in a sample, comprising the probe of claim 1, a FEN nuclease, and packaging material therefore.

44. The kit of claim 43, further comprising a suitable buffer.

45. The kit of claim 43, further comprising a nucleic acid polymerase substantially lacking 5' to 3' exonuclease activity.

46. The kit of claim 43, further comprising a primer.

47. A kit for generating a signal indicative of the presence of a target nucleic acid sequence in a sample, comprising the probe of claim 1, a primer, and packaging material therefore.

48. The kit of claim 47, further comprising a suitable buffer.

49. The kit of claim 47, further comprising a nucleic acid polymerase substantially lacking 5' to 3' exonuclease activity.

50. The kit of claim 47, further comprising a FEN nuclease.

51. The probe of claim 1, wherein the detectable signal emitted by one of said pair of labels is substantially constant upon binding of said probe to target nucleic acid.

52. The probe of claim 28, wherein the detectable signal emitted by one of said pair of labels is substantially constant upon binding of said probe to target nucleic acid.

53. The probe of claim 29, wherein the detectable signal by one of said pair of labels is substantially constant upon binding of said probe to target nucleic acid.

54. The probe of claim 28, further comprising a linker sequence, located between said hairpin sequence and said target binding sequence.

55. The probe of claim 28, wherein said pair comprises a fluorophore and a quencher.

* * * * *

SEQUENCE LISTING

<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide probe for murine
      TFIID mRNA detection

<400> SEQUENCE: 1
tgcgtttttc gcattgtgca caggagccaa gagtgaaga                                39

<210> SEQ ID NO 2
<211> LENGTH: 38
<212> TYPE: DNA
<213> ORGANISM: Artificial Sequence
<220> FEATURE:
<223> OTHER INFORMATION: Synthetic oligonucleotide probe for detection
      of TNF-alpha mRNA

<400> SEQUENCE: 2
tgcgtttttc gcatacaggc agccagctgt tcctcctt                                 38

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide probe to detect
      TNF-alpha mRNA

<400> SEQUENCE: 3
tgcgtttttc gcatttacag gcagccagct gttcctcctt                               40